(12) United States Patent
Lopez et al.

(10) Patent No.: US 8,277,418 B2
(45) Date of Patent: Oct. 2, 2012

(54) OPHTHALMIC VALVED TROCAR CANNULA

(75) Inventors: Jose Luis Lopez, Cypress, CA (US); Michael M. Martin, Newport Beach, CA (US); Anil K. Patnala, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 12/951,266

(22) Filed: Nov. 22, 2010

(65) Prior Publication Data

US 2011/0152774 A1    Jun. 23, 2011

Related U.S. Application Data

(60) Provisional application No. 61/289,449, filed on Dec. 23, 2009.

(51) Int. Cl.
*A61M 5/178*    (2006.01)
(52) U.S. Cl. .................................. 604/165.04
(58) Field of Classification Search .............. 604/165.04
See application file for complete search history.

(56) References Cited

U.S. PATENT DOCUMENTS

| | | | |
|---|---|---|---|
| 1,198,742 A | 9/1916 | Mienecke | |
| 2,922,420 A | 1/1960 | Cheng | |
| 3,190,661 A | 6/1965 | Wahl et al. | |
| 3,308,819 A | 3/1967 | Arp | |
| 3,313,299 A | 4/1967 | Spademan | |
| 3,461,869 A | 8/1969 | Hargest | |
| 3,510,177 A | 5/1970 | Shimula | |
| 3,528,410 A | 9/1970 | Banko | |
| 3,528,425 A | 9/1970 | Banko | |
| 3,547,119 A | 12/1970 | Hall et al. | |
| 3,568,436 A | 3/1971 | Heffner et al. | |
| 3,611,965 A | 10/1971 | Lange | |
| 3,638,649 A | 2/1972 | Ersek | |

(Continued)

FOREIGN PATENT DOCUMENTS

CA    1225299 A2    8/1987

(Continued)

OTHER PUBLICATIONS

Eckardt, Claus, "Transconjunctival Sutureless 23-Gauge Citrectomy," Retina, the Journal of Retinal and Vitreous Diseases, vol. 25, Nov. 2, 2005.

(Continued)

*Primary Examiner* — Christopher D Koharski
*Assistant Examiner* — Jason Flick
(74) *Attorney, Agent, or Firm* — Russell Henrichs (57) ABSTRACT

In various embodiments, a trocar cannula may be configured for insertion into an eye to facilitate insertion and removal of instruments during surgery. The cannula may be affixed to an overcap (to inhibit rotation of the overcap relative to the cannula) that includes a seal. In some embodiments, the seal may be overmolded into the overcap or may include a wafer that is fixed between the cannula and the overcap to inhibit rotation relative to the cannula and the overcap. In some embodiments, the cannula and overcap may snap together through a tab/slot interface in a permanent fashion such that the cannula and overcap may not be separated without damaging the cannula or overcap. In some embodiments, a vent cannula may be receivable in the slit of the seal for allowing fluids to vent from the eye through the cannula (which may include an indentation to frictionally engage the vent).

15 Claims, 11 Drawing Sheets

U.S. PATENT DOCUMENTS

| | | |
|---|---|---|
| 3,659,607 A | 5/1972 | Banko |
| 3,774,612 A | 11/1973 | Marco |
| 3,776,238 A | 12/1973 | Peyman et al. |
| 3,788,327 A | 1/1974 | Donowitz et al. |
| 3,815,604 A | 6/1974 | O'Malley et al. |
| 3,829,104 A | 8/1974 | Green |
| 3,853,127 A | 12/1974 | Spademan |
| 3,884,237 A | 5/1975 | O'Malley et al. |
| 3,884,238 A | 5/1975 | O'Malley et al. |
| 4,011,869 A | 3/1977 | Seiler, Jr. |
| 4,135,516 A | 1/1979 | Spina et al. |
| 4,146,237 A | 3/1979 | Bergman |
| 4,177,814 A | 12/1979 | Knepshield et al. |
| 4,200,106 A | 4/1980 | Dinkelkamp et al. |
| 4,222,575 A | 9/1980 | Sekiguchi et al. |
| 4,295,821 A | 10/1981 | Schilling |
| 4,299,217 A | 11/1981 | Sagae et al. |
| 4,331,130 A | 5/1982 | Lewicky |
| 4,340,037 A | 7/1982 | Lewicky |
| 4,386,927 A | 6/1983 | Eichenbaum |
| 4,387,879 A | 6/1983 | Tauschinski |
| 4,395,258 A | 7/1983 | Wang et al. |
| 4,413,829 A | 11/1983 | Pietsch |
| 4,470,268 A | 9/1984 | Schilling |
| 4,493,698 A | 1/1985 | Wang et al. |
| 4,530,359 A | 7/1985 | Helfgott et al. |
| 4,551,129 A | 11/1985 | Coleman et al. |
| 4,565,544 A | 1/1986 | Muller et al. |
| 4,573,979 A | 3/1986 | Blake |
| 4,590,935 A | 5/1986 | Ranalli |
| 4,610,665 A | 9/1986 | Matsumoto et al. |
| 4,617,018 A | 10/1986 | Nishi |
| 4,642,090 A | 2/1987 | Utrata |
| 4,650,460 A | 3/1987 | Roizenblatt |
| 4,655,743 A | 4/1987 | Hyde |
| 4,655,752 A | 4/1987 | Honkanen et al. |
| 4,670,006 A | 6/1987 | Sinnett et al. |
| 4,674,502 A | 6/1987 | Imonti et al. |
| 4,689,047 A | 8/1987 | Bauer |
| 4,692,142 A | 9/1987 | Dignam et al. |
| 4,693,343 A | 9/1987 | Boyd |
| 4,696,298 A | 9/1987 | Higgins et al. |
| 4,699,140 A | 10/1987 | Holmes et al. |
| 4,702,244 A | 10/1987 | Mazzocco |
| 4,705,511 A | 11/1987 | Kocak |
| 4,753,234 A | 6/1988 | Martinez |
| 4,755,173 A | 7/1988 | Konopka et al. |
| 4,756,536 A | 7/1988 | Belcher |
| 4,759,746 A | 7/1988 | Straus |
| 4,772,261 A | 9/1988 | Von Hoff et al. |
| 4,772,264 A | 9/1988 | Cragg |
| 4,781,675 A | 11/1988 | White |
| 4,795,446 A | 1/1989 | Fecht |
| 4,808,158 A | 2/1989 | Kreuzer et al. |
| 4,808,170 A | 2/1989 | Thornton et al. |
| 4,817,631 A | 4/1989 | Schnepp-Pesch et al. |
| 4,819,635 A | 4/1989 | Shapiro |
| 4,820,264 A | 4/1989 | Matsui et al. |
| 4,846,172 A | 7/1989 | Berlin |
| 4,850,406 A | 7/1989 | Krautzberger |
| 4,863,432 A | 9/1989 | Kralo |
| 4,869,718 A | 9/1989 | Brader |
| 4,894,057 A | 1/1990 | Howes |
| 4,894,657 A | 1/1990 | Hwang et al. |
| 4,908,015 A | 3/1990 | Anis |
| 4,911,161 A | 3/1990 | Schechter |
| 4,935,010 A | 6/1990 | Cox et al. |
| 4,940,468 A | 7/1990 | Petillo |
| 4,959,057 A | 9/1990 | Lang |
| 4,968,296 A | 11/1990 | Ritch et al. |
| 5,009,435 A | 4/1991 | Villanyi et al. |
| 5,019,035 A | 5/1991 | Missirlian et al. |
| 5,037,384 A | 8/1991 | Chang |
| 5,041,095 A | 8/1991 | Littrell |
| 5,053,013 A | 10/1991 | Ensminger et al. |
| 5,057,082 A | 10/1991 | Burchette, Jr. |
| 5,057,098 A | 10/1991 | Zelman |
| 5,092,837 A | 3/1992 | Ritch et al. |
| 5,098,443 A | 3/1992 | Parel et al. |
| 5,106,376 A | 4/1992 | Mononen et al. |
| 5,147,316 A | 9/1992 | Castillenti |
| 5,149,327 A | 9/1992 | Oshiyama |
| 5,176,628 A | 1/1993 | Charles et al. |
| 5,176,652 A | 1/1993 | Littrell |
| 5,176,662 A | 1/1993 | Bartholomew et al. |
| 5,197,457 A | 3/1993 | Adair |
| 5,215,526 A | 6/1993 | Deniega et al. |
| 5,217,441 A | 6/1993 | Schichman |
| 5,219,278 A | 6/1993 | Van Lintel |
| 5,219,361 A | 6/1993 | von Recum et al. |
| 5,226,890 A | 7/1993 | Ianniruberto et al. |
| 5,244,924 A | 9/1993 | Meinert |
| 5,257,996 A | 11/1993 | McGuire |
| 5,284,472 A | 2/1994 | Sussman et al. |
| 5,330,501 A | 7/1994 | Torey et al. |
| 5,333,606 A | 8/1994 | Schneider et al. |
| 5,334,163 A | 8/1994 | Sinnett |
| 5,336,175 A | 8/1994 | Mames |
| 5,346,491 A | 9/1994 | Oertli |
| 5,364,365 A | 11/1994 | Wortrich |
| 5,368,015 A | 11/1994 | Wilk |
| 5,380,288 A | 1/1995 | Hart et al. |
| 5,383,877 A | 1/1995 | Clarke |
| 5,385,553 A | 1/1995 | Hart et al. |
| 5,389,077 A | 2/1995 | Melinyshyn et al. |
| 5,397,805 A | 3/1995 | Meinert |
| 5,407,427 A | 4/1995 | Zhu et al. |
| 5,407,441 A | 4/1995 | Greenbaum |
| 5,425,730 A | 6/1995 | Luloh |
| 5,432,151 A | 7/1995 | Russo et al. |
| 5,437,644 A | 8/1995 | Nobles |
| 5,441,487 A | 8/1995 | Vedder |
| 5,443,452 A | 8/1995 | Hart et al. |
| 5,456,284 A | 10/1995 | Ryan et al. |
| 5,478,329 A | 12/1995 | Ternamian |
| 5,487,725 A | 1/1996 | Peyman |
| 5,496,289 A | 3/1996 | Wenstrom, Jr. |
| 5,538,509 A | 7/1996 | Dunlap et al. |
| 5,545,153 A | 8/1996 | Grinblat et al. |
| 5,547,473 A | 8/1996 | Peyman |
| 5,558,142 A | 9/1996 | Ehrle et al. |
| 5,569,206 A | 10/1996 | Gorman et al. |
| 5,580,347 A | 12/1996 | Reimels |
| 5,591,137 A | 1/1997 | Stevens |
| 5,607,441 A | 3/1997 | Sierocuk et al. |
| 5,630,809 A | 5/1997 | Connor |
| 5,630,827 A | 5/1997 | Vijfvinkel et al. |
| 5,643,250 A | 7/1997 | O'Donnell, Jr. |
| 5,697,898 A | 12/1997 | Devine |
| 5,697,947 A | 12/1997 | Wolf et al. |
| 5,702,370 A | 12/1997 | Sylvanowicz et al. |
| 5,707,643 A | 1/1998 | Ogura et al. |
| 5,716,363 A | 2/1998 | Josephberg |
| 5,725,514 A | 3/1998 | Grinblat et al. |
| 5,728,121 A | 3/1998 | Bimbo et al. |
| 5,738,628 A | 4/1998 | Sierocuk et al. |
| 5,752,938 A | 5/1998 | Flatland et al. |
| 5,752,970 A | 5/1998 | Yoon |
| 5,755,700 A | 5/1998 | Kritzinger et al. |
| 5,767,079 A | 6/1998 | Glaser et al. |
| 5,782,813 A | 7/1998 | Yoon |
| 5,800,406 A | 9/1998 | Kritzinger et al. |
| 5,800,451 A | 9/1998 | Buess et al. |
| 5,803,919 A | 9/1998 | Hart et al. |
| 5,807,338 A | 9/1998 | Smith et al. |
| 5,810,863 A | 9/1998 | Wolf et al. |
| 5,817,049 A | 10/1998 | Edwards |
| 5,817,061 A | 10/1998 | Goodwin et al. |
| 5,817,062 A | 10/1998 | Flom et al. |
| 5,817,099 A | 10/1998 | Skolik et al. |
| 5,820,604 A | 10/1998 | Fox et al. |
| 5,824,002 A | 10/1998 | Gentelia et al. |
| 5,843,111 A | 12/1998 | Vijfvinkel |
| 5,846,258 A | 12/1998 | Takayanagi et al. |
| 5,848,987 A | 12/1998 | Baudino et al. |
| 5,853,579 A | 12/1998 | Rummler et al. |
| 5,865,807 A | 2/1999 | Blake, III |

| | | | | | | | |
|---|---|---|---|---|---|---|---|
| 5,879,333 | A | 3/1999 | Smith | 6,569,118 | B2 | 5/2003 | Johnson et al. |
| 5,879,338 | A | 3/1999 | Mahurkar | 6,575,040 | B2 | 6/2003 | Dietrich |
| 5,885,217 | A | 3/1999 | Gisselberg et al. | 6,575,990 | B1 | 6/2003 | Wang et al. |
| 5,885,252 | A | 3/1999 | Liu | 6,579,267 | B2 | 6/2003 | Lynch et al. |
| 5,885,253 | A | 3/1999 | Liu | 6,579,281 | B2 | 6/2003 | Palmer et al. |
| 5,906,584 | A | 5/1999 | Pavoni et al. | D477,869 | S | 7/2003 | Vijfvinkel |
| 5,911,699 | A | 6/1999 | Anis et al. | 6,585,972 | B2 | 7/2003 | Peyman |
| 5,916,198 | A | 6/1999 | Dillow | 6,589,208 | B2 | 7/2003 | Ewers et al. |
| 5,919,158 | A | 7/1999 | Saperstein et al. | 6,599,271 | B1 | 7/2003 | Easley |
| 5,928,198 | A | 7/1999 | Lester | 6,610,031 | B1 | 8/2003 | Chin |
| 5,935,107 | A | 8/1999 | Taylor et al. | 6,632,200 | B2 | 10/2003 | Guo et al. |
| 5,947,990 | A | 9/1999 | Smith et al. | 6,638,253 | B2 | 10/2003 | Breznock |
| 5,957,898 | A | 9/1999 | Jepson et al. | 6,666,844 | B1 | 12/2003 | Igo et al. |
| 5,968,058 | A | 10/1999 | Richter et al. | 6,666,846 | B1 | 12/2003 | Turovskiy et al. |
| 5,979,494 | A | 11/1999 | Perkins et al. | 6,669,708 | B1 | 12/2003 | Nissenbaum et al. |
| 5,984,896 | A | 11/1999 | Boyd | 6,706,009 | B2 | 3/2004 | Diermann et al. |
| 5,984,913 | A | 11/1999 | Kritzinger et al. | 6,706,275 | B1 | 3/2004 | Camp |
| 5,988,824 | A | 11/1999 | Rowsey, Jr. | 6,743,207 | B2 | 6/2004 | Elbert et al. |
| 5,993,471 | A | 11/1999 | Riza et al. | 6,749,595 | B1 | 6/2004 | Murphy |
| 5,997,528 | A | 12/1999 | Bisch et al. | 6,764,439 | B2 | 7/2004 | Schaaf et al. |
| 5,997,560 | A | 12/1999 | Miller | 6,800,076 | B2 | 10/2004 | Humayun |
| 6,004,302 | A | 12/1999 | Brierley | 6,808,505 | B2 | 10/2004 | Kadan |
| 6,007,513 | A | 12/1999 | Anis et al. | 6,827,683 | B2 | 12/2004 | Otawara |
| 6,019,472 | A | 2/2000 | Koester et al. | 6,846,318 | B2 | 1/2005 | Camp |
| 6,027,493 | A | 2/2000 | Donitzky et al. | 6,872,198 | B1 | 3/2005 | Wilson et al. |
| 6,045,535 | A | 4/2000 | Ben Nunn | D504,176 | S | 4/2005 | Vijfvinkel |
| 6,055,458 | A | 4/2000 | Cochran et al. | 6,875,165 | B2 | 4/2005 | de Juan, Jr. et al. |
| 6,086,570 | A | 7/2000 | Aboul-Hosn et al. | 6,878,110 | B2 | 4/2005 | Yang et al. |
| 6,099,505 | A * | 8/2000 | Ryan et al. ............... 604/167.04 | 6,887,194 | B2 | 5/2005 | Hart et al. |
| 6,099,544 | A | 8/2000 | Wolf et al. | 6,899,717 | B2 | 5/2005 | Weber et al. |
| 6,120,147 | A | 9/2000 | Vijfvinkel et al. | 6,899,877 | B2 | 5/2005 | Peyman |
| 6,120,518 | A | 9/2000 | Mark et al. | 6,902,577 | B2 | 6/2005 | Lipshitz et al. |
| 6,123,689 | A | 9/2000 | To et al. | 6,916,310 | B2 | 7/2005 | Sommerich |
| 6,139,560 | A | 10/2000 | Kremer | 6,936,053 | B1 | 8/2005 | Weiss |
| 6,146,378 | A | 11/2000 | Mikus et al. | 6,939,299 | B1 | 9/2005 | Peterson et al. |
| 6,162,221 | A | 12/2000 | Ouchi | 6,939,341 | B2 | 9/2005 | Vijfvinkel |
| 6,171,299 | B1 | 1/2001 | Bonutti | 6,989,003 | B2 | 1/2006 | Wing et al. |
| 6,203,518 | B1 | 3/2001 | Anis et al. | 6,997,907 | B2 | 2/2006 | Safabash et al. |
| 6,213,988 | B1 | 4/2001 | McIvor et al. | 7,008,404 | B2 | 3/2006 | Nakajima |
| 6,217,543 | B1 | 4/2001 | Anis et al. | 7,011,647 | B2 | 3/2006 | Purdy et al. |
| 6,228,022 | B1 | 5/2001 | Freisem et al. | 7,025,747 | B2 | 4/2006 | Smith |
| 6,228,071 | B1 | 5/2001 | Moshe et al. | 7,048,718 | B1 | 5/2006 | Mithiue et al. |
| 6,231,549 | B1 | 5/2001 | Noecker et al. | 7,066,927 | B2 | 6/2006 | Chen et al. |
| 6,238,407 | B1 | 5/2001 | Wolf et al. | 7,074,426 | B2 | 7/2006 | Kochinke |
| 6,251,103 | B1 | 6/2001 | Berlin | 7,077,848 | B1 | 7/2006 | de Juan, Jr. et al. |
| 6,273,894 | B1 | 8/2001 | Dykes | 7,090,681 | B2 | 8/2006 | Weber et al. |
| 6,290,690 | B1 | 9/2001 | Huculak et al. | 7,115,114 | B2 | 10/2006 | Caizza |
| 6,340,361 | B1 | 1/2002 | Kraus et al. | 7,144,386 | B2 | 12/2006 | Korkor et al. |
| 6,344,038 | B1 | 2/2002 | Weber | 7,147,644 | B2 | 12/2006 | Weber et al. |
| 6,352,519 | B1 | 3/2002 | Anis et al. | 7,160,309 | B2 | 1/2007 | Voss |
| 6,355,028 | B2 | 3/2002 | Casteneda et al. | 7,172,577 | B2 | 2/2007 | Mangano et al. |
| 6,371,964 | B1 | 4/2002 | Vargas et al. | 7,172,612 | B2 | 2/2007 | Ishikawa et al. |
| 6,378,526 | B1 | 4/2002 | Bowman et al. | 7,217,263 | B2 | 5/2007 | Humayun et al. |
| 6,397,849 | B1 | 6/2002 | Bowman et al. | 7,220,225 | B2 | 5/2007 | de Juan, Jr. et al. |
| 6,402,734 | B1 | 6/2002 | Weiss | 7,223,225 | B2 | 5/2007 | de Juan, Jr. et al. |
| 6,412,946 | B1 | 7/2002 | Vijfvinkel et al. | 7,226,435 | B2 | 6/2007 | Darnell |
| 6,413,245 | B1 | 7/2002 | Yaacobi et al. | 7,229,433 | B2 | 6/2007 | Mullen |
| 6,419,627 | B1 | 7/2002 | Ben Nunn | 7,276,019 | B2 | 10/2007 | de Juan, Jr. et al. |
| 6,419,654 | B1 | 7/2002 | Kadan | 7,285,107 | B1 | 10/2007 | Charles |
| 6,423,036 | B1 | 7/2002 | Van Huizen | 7,294,140 | B2 | 11/2007 | Mosnier et al. |
| 6,428,502 | B1 | 8/2002 | Lang | 7,297,138 | B2 | 11/2007 | Fangrow, Jr. |
| 6,432,085 | B1 | 8/2002 | Stellon et al. | 7,338,477 | B2 | 3/2008 | Meyer et al. |
| 6,439,541 | B1 | 8/2002 | Nosel et al. | 7,354,416 | B2 | 4/2008 | Quiroz-Mercado et al. |
| 6,451,041 | B1 | 9/2002 | Moenning et al. | 7,361,158 | B1 | 4/2008 | Mooney, Jr. |
| 6,464,691 | B1 | 10/2002 | Casteneda et al. | 7,390,317 | B2 | 6/2008 | Taylor et al. |
| 6,471,666 | B1 | 10/2002 | Odrich | 7,402,156 | B2 | 7/2008 | Kiehlbauch et al. |
| 6,478,806 | B2 | 11/2002 | McFarlane | 7,413,560 | B2 | 8/2008 | Chong et al. |
| 6,482,182 | B1 | 11/2002 | Carroll et al. | 7,429,259 | B2 | 9/2008 | Cadeddu et al. |
| 6,488,662 | B2 | 12/2002 | Sirimanne | 7,442,686 | B2 | 10/2008 | Lasko et al. |
| 6,506,181 | B2 | 1/2003 | Meng et al. | 7,468,065 | B2 | 12/2008 | Weber et al. |
| 6,508,786 | B2 | 1/2003 | Huitema et al. | 7,481,795 | B2 | 1/2009 | Thompson et al. |
| 6,511,454 | B1 | 1/2003 | Nakao et al. | 7,485,113 | B2 | 2/2009 | Varner et al. |
| 6,520,938 | B1 | 2/2003 | Funderburk et al. | 7,524,305 | B2 | 4/2009 | Moyer |
| 6,546,280 | B2 | 4/2003 | Osborne | 7,524,310 | B2 | 4/2009 | Meyer et al. |
| 6,551,291 | B1 | 4/2003 | de Juan, Jr. et al. | 7,537,593 | B2 | 5/2009 | Humayun |
| 6,558,342 | B1 | 5/2003 | Yaron et al. | 7,604,647 | B2 | 10/2009 | Chen |
| 6,561,519 | B1 | 5/2003 | Frese et al. | 7,611,492 | B2 | 11/2009 | Sonoda et al. |
| 6,561,999 | B1 | 5/2003 | Nazarifar et al. | 7,622,628 | B2 | 11/2009 | Bergin et al. |
| 6,562,005 | B1 | 5/2003 | Donath | 7,637,863 | B2 | 12/2009 | Deal et al. |

| | | |
|---|---|---|
| 7,648,494 B2 | 1/2010 | Kornerup et al. |
| 7,783,346 B2 | 8/2010 | Smith et al. |
| 7,947,018 B2 * | 5/2011 | McKinnon ............... 604/167.03 |
| 2001/0053573 A1 | 12/2001 | Lee |
| 2002/0002362 A1 | 1/2002 | Humayun et al. |
| 2002/0010424 A1 | 1/2002 | Dennis et al. |
| 2002/0013597 A1 | 1/2002 | McFarlane |
| 2002/0038122 A1 | 3/2002 | Peters |
| 2002/0072673 A1 | 6/2002 | Yamamoto et al. |
| 2002/0087128 A1 | 7/2002 | Paques et al. |
| 2002/0099420 A1 | 7/2002 | Chow et al. |
| 2002/0198511 A1 | 12/2002 | Varner et al. |
| 2003/0093132 A1 | 5/2003 | Eckmiller |
| 2003/0169603 A1 | 9/2003 | Luloh et al. |
| 2003/0171722 A1 | 9/2003 | Paques et al. |
| 2004/0039667 A1 | 2/2004 | Winklevoss et al. |
| 2004/0054374 A1 | 3/2004 | Weber et al. |
| 2004/0073231 A1 | 4/2004 | de Juan, Jr. et al. |
| 2004/0092982 A1 | 5/2004 | Sheffer |
| 2004/0117202 A1 | 6/2004 | Winklevoss et al. |
| 2004/0153021 A1 | 8/2004 | Osborne et al. |
| 2004/0215133 A1 | 10/2004 | Weber et al. |
| 2004/0249454 A1 | 12/2004 | Terwee |
| 2004/0254517 A1 | 12/2004 | Quiroz-Mercado et al. |
| 2005/0085774 A1 | 4/2005 | Streifinger et al. |
| 2005/0101967 A1 | 5/2005 | Weber et al. |
| 2005/0107734 A1 | 5/2005 | Coroneo |
| 2005/0148949 A1 | 7/2005 | Thumann |
| 2005/0148957 A1 | 7/2005 | Girard et al. |
| 2005/0149078 A1 | 7/2005 | Vargas et al. |
| 2005/0154399 A1 | 7/2005 | Weber et al. |
| 2005/0177019 A1 | 8/2005 | de Juan, Jr. et al. |
| 2005/0191322 A1 | 9/2005 | Norrby |
| 2005/0192537 A1 | 9/2005 | Osborne et al. |
| 2005/0203333 A1 | 9/2005 | Dailey et al. |
| 2005/0203542 A1 | 9/2005 | Weber et al. |
| 2005/0281861 A1 | 12/2005 | Hughes et al. |
| 2005/0288697 A1 | 12/2005 | Tei et al. |
| 2006/0047250 A1 | 3/2006 | Hickingbotham et al. |
| 2006/0047255 A1 | 3/2006 | Kiehlbauch et al. |
| 2006/0084921 A1 | 4/2006 | Darnell |
| 2006/0086711 A1 | 4/2006 | Deason et al. |
| 2006/0089526 A1 * | 4/2006 | Chen et al. .................... 600/101 |
| 2006/0089607 A1 | 4/2006 | Chen |
| 2006/0103233 A1 | 5/2006 | Lenz |
| 2006/0106415 A1 | 5/2006 | Gabbay |
| 2006/0111605 A1 | 5/2006 | Larsen et al. |
| 2006/0142699 A1 | 6/2006 | Lampropoulos |
| 2006/0149194 A1 | 7/2006 | Conston et al. |
| 2006/0173413 A1 | 8/2006 | Fan |
| 2006/0184162 A1 | 8/2006 | Smith |
| 2006/0189915 A1 | 8/2006 | Camras et al. |
| 2006/0200097 A1 | 9/2006 | Humayun et al. |
| 2006/0212061 A1 | 9/2006 | Wenchell |
| 2006/0217655 A1 | 9/2006 | Vitullo et al. |
| 2006/0241650 A1 | 10/2006 | Weber et al. |
| 2006/0270989 A1 | 11/2006 | McMichael et al. |
| 2006/0271078 A1 | 11/2006 | Modesitt |
| 2006/0276738 A1 | 12/2006 | Becker |
| 2007/0016137 A1 | 1/2007 | Attinger |
| 2007/0021762 A1 | 1/2007 | Liu et al. |
| 2007/0027452 A1 | 2/2007 | Varner et al. |
| 2007/0027470 A1 | 2/2007 | Dodick |
| 2007/0055089 A1 | 3/2007 | Larsen et al. |
| 2007/0059336 A1 | 3/2007 | Hughes et al. |
| 2007/0106235 A1 | 5/2007 | Coroneo |
| 2007/0106236 A1 | 5/2007 | Coroneo |
| 2007/0106300 A1 | 5/2007 | Auld et al. |
| 2007/0106301 A1 | 5/2007 | Charles et al. |
| 2007/0106319 A1 | 5/2007 | Au et al. |
| 2007/0179512 A1 | 8/2007 | Olsen |
| 2007/0198045 A1 | 8/2007 | Morton et al. |
| 2007/0213691 A1 | 9/2007 | Summerer et al. |
| 2007/0244442 A1 | 10/2007 | Chowhan |
| 2007/0287962 A1 | 12/2007 | Watanabe et al. |
| 2007/0293873 A1 | 12/2007 | Chang |
| 2008/0011225 A1 | 1/2008 | McClure et al. |
| 2008/0015417 A1 | 1/2008 | Hawkes et al. |
| 2008/0021399 A1 | 1/2008 | Spaide |
| 2008/0033351 A1 | 2/2008 | Trogden et al. |
| 2008/0033462 A1 | 2/2008 | Di Nardo et al. |
| 2008/0058761 A1 | 3/2008 | Spaide |
| 2008/0076960 A1 | 3/2008 | Marseille et al. |
| 2008/0077120 A1 | 3/2008 | Vijfvinkel |
| 2008/0097335 A1 | 4/2008 | Trogden et al. |
| 2008/0097346 A1 | 4/2008 | Charles |
| 2008/0097418 A1 | 4/2008 | Jones et al. |
| 2008/0097420 A1 | 4/2008 | Vijfvinkel et al. |
| 2008/0154204 A1 | 6/2008 | Varner et al. |
| 2008/0161845 A1 | 7/2008 | Murakami et al. |
| 2008/0171989 A1 | 7/2008 | Bell et al. |
| 2008/0172009 A1 | 7/2008 | Attinger |
| 2008/0177239 A1 | 7/2008 | Li et al. |
| 2008/0188811 A1 | 8/2008 | Kim |
| 2008/0188910 A1 | 8/2008 | Spaide |
| 2008/0195044 A1 | 8/2008 | Nishimura |
| 2008/0195135 A1 | 8/2008 | Attinger |
| 2008/0215078 A1 | 9/2008 | Bennett |
| 2008/0228127 A1 | 9/2008 | Burns et al. |
| 2008/0266520 A1 | 10/2008 | Spaide |
| 2008/0273172 A1 | 11/2008 | Spaide |
| 2008/0281277 A1 | 11/2008 | Thyzel |
| 2008/0281292 A1 | 11/2008 | Hickingbotham et al. |
| 2008/0306428 A1 | 12/2008 | Becket |
| 2008/0306442 A1 | 12/2008 | Bardsley et al. |
| 2008/0312662 A1 * | 12/2008 | Hickingbotham ............ 606/107 |
| 2009/0018507 A1 | 1/2009 | Schmitz et al. |
| 2009/0036827 A1 | 2/2009 | Cazzini |
| 2009/0036878 A1 | 2/2009 | Vijfvinkel et al. |
| 2009/0076463 A1 | 3/2009 | Attinger |
| 2009/0118703 A1 | 5/2009 | Orilla et al. |
| 2009/0125057 A1 | 5/2009 | Cordova |
| 2009/0132040 A1 | 5/2009 | Frion et al. |
| 2009/0138022 A1 | 5/2009 | Tu et al. |
| 2009/0138043 A1 | 5/2009 | Kohm |
| 2009/0143763 A1 | 6/2009 | Wyss et al. |
| 2009/0163862 A1 | 6/2009 | Kauphusman et al. |
| 2009/0171293 A1 | 7/2009 | Yang et al. |
| 2009/0171326 A1 | 7/2009 | Hohla et al. |
| 2009/0182279 A1 | 7/2009 | Wenchell et al. |
| 2009/0192464 A1 | 7/2009 | Axelsson et al. |
| 2009/0192465 A1 | 7/2009 | Smith |
| 2009/0196903 A1 | 8/2009 | Kliman |
| 2009/0221966 A1 | 9/2009 | Richard |
| 2009/0227934 A1 | 9/2009 | Euteneuer et al. |
| 2009/0234292 A1 | 9/2009 | Di Nardo et al. |
| 2009/0306591 A1 | 12/2009 | Amisar et al. |
| 2009/0312662 A1 | 12/2009 | Colman et al. |
| 2009/0318866 A1 | 12/2009 | Ferrari |
| 2009/0326461 A1 | 12/2009 | Gresham |
| 2010/0057010 A1 | 3/2010 | Goransson |
| 2010/0057011 A1 | 3/2010 | Charles |
| 2011/0015658 A1 | 1/2011 | Vijfvinkel |

FOREIGN PATENT DOCUMENTS

| | | |
|---|---|---|
| CA | 2138247 C | 8/2006 |
| DE | 6808511 U | 8/1969 |
| DE | 29710025 U1 | 8/1997 |
| EP | 0564373 A1 | 10/1993 |
| EP | 0791336 A1 | 8/1997 |
| EP | 0972493 A2 | 1/2000 |
| EP | 0972493 A3 | 3/2000 |
| EP | 0972493 B1 | 6/2005 |
| EP | 1886653 A1 | 2/2008 |
| EP | 1923010 A1 | 5/2008 |
| EP | 2002812 A1 | 12/2008 |
| EP | 2103265 A1 | 9/2009 |
| FR | 2710270 A1 | 3/1995 |
| FR | 2727849 A1 | 6/1996 |
| GB | 2156223 A | 10/1989 |
| GB | 2352183 A | 1/2001 |
| GB | 2352183 B | 3/2003 |
| JP | 7146387 A | 6/1995 |
| JP | 2007-319423 A | 12/2007 |
| JP | 2009-219879 A | 10/2009 |
| NL | 2001401 C2 | 9/2009 |
| SU | 1706611 A1 | 1/1992 |
| WO | WO 90/15415 A1 | 12/1990 |

| | | |
|---|---|---|
| WO | WO 92/19143 A2 | 11/1992 |
| WO | WO 93/00683 A1 | 1/1993 |
| WO | WO 93/05716 A1 | 4/1993 |
| WO | WO 93/05719 A1 | 4/1993 |
| WO | WO 96/23536 A1 | 8/1996 |
| WO | WO 01/15640 A1 | 3/2001 |
| WO | WO 01/68016 A2 | 9/2001 |
| WO | WO 01/68016 A3 | 7/2002 |
| WO | WO 2005/017918 A2 | 2/2005 |
| WO | WO 2005/086693 A2 | 9/2005 |
| WO | WO 2005/017918 A3 | 1/2006 |
| WO | WO 2006/086711 A1 | 8/2006 |
| WO | WO 2006/103233 A1 | 10/2006 |
| WO | WO 2007/093957 A2 | 8/2007 |
| WO | WO 2007/093957 A3 | 11/2007 |
| WO | WO 2008/011225 A2 | 1/2008 |
| WO | WO 2008/011225 A3 | 2/2009 |
| WO | WO 2005/086693 A3 | 4/2009 |
| WO | WO 2009/120075 A1 | 10/2009 |
| WO | WO 2009/124406 A1 | 10/2009 |
| WO | WO 2010/064062 A1 | 6/2010 |
| WO | WO 2011/087577 A1 | 7/2011 |

OTHER PUBLICATIONS

Hagemann, L.F., et al., "How to Create an Immediate Self Sealing Sclerotomy for Cannula Placement in 25 Gauge Vitrectomy Using a Tunnel Incision," Abstract; Investigative Ophthalmology and Visual Science, 2005.

McCary, et al.., "Millennium™ TSV25: System Enhancements Bring Added Safety, Efficiency and Ease-of-Use to 25-Gauge Vitrectomy," 2004 Copyright obtained from a www.finelinescom.com website.

Cacciatori, Matteo, et al., "Injection of Gas Mixture During Pars Plana Vitrectomy: Surgical Technique," Techniques in Ophthalmology 5(4), 2007.

Flynn, Harry, et al., "Design features and surgical use of a cannulated extrusion needle," Graefe's Archive Ophthalmology, p. 304, 1989.

McLeod, David, et al., "Modified Charles flute needle," British Journal of Ophthalmology, p. 69, 1981.

MedOne Broshure, downloaded from http://www.medone.com/retinal_cannulas_accessories.html on Mar. 3, 2011; Copyright 2009.

Fujii, Gildo, et al., "Initial Experience Using the Transconjunctival Sutureless Vitrectomy System for Vitreoretinal Surgery," American Academy of Ophthalmology, copyright 2002.

Lopez-Guajardo, Lorenzo, et al., "Oblique Sclerotomy Technique for Prevention of Incompetent Wound Closure in Transconjunctival 25-Guage Vitrectomy," American Journal of Ophthalmology, Jun. 2006.

ALCON®, "Constellation® VFC Pak," Vitreoretinal Product Catalog, p. 6, 2008, 2 pgs.

DORC: Focus on Precision Catalog, Copyright 2008.

DORC: The highlights Catalog: Copyright 2006.

"The autoseal Pars Plana Microincision System from Oertli Instruments: How you can get Swiss watchmaker technology into a trocar;" ApplicationNote, Feb. 2008.

"ACCURUS® Surgical System 25-Gauge Instruments Portfolio," Alcon, Inc., 2005, 6 pgs.

Groves, N., "More surgeons adopting 25-gauge vitrectomy technique," Ophthalmology Times, Jun. 2005, 5 pgs.

Groves, N., "Tools for 25-gauge vitrectomy open door for other procedures," Ophthalmology Times, 30:12, Jun. 2005, 2 pgs.

Riemann, C., "Expanding the Options for 25-ga. Vitrectomy," Review of Ophthalmology, Feb. 2005, 3 pgs.

Charters, L., "Tackling complex retinal surgery possible with smaller instrumentation," Ophthalmology Time, 31:8, Apr. 2006, 1 pg.

Roe, R.H., et al., "Small-Gauge Vitrectomy: The Future is Now," Rev. of Ophthalmology, 14:06, Jun. 1, 2007, 4 pgs.

Prosecution History of U.S. Appl. No. 11/762,238, filed Jun. 13, 2007, 108 pages.

Huculak, John C., et al., "Ophthalmic Valved Trocar Vent," U.S. Appl. No. 12/951,272, filed Nov. 22, 2010, 29 pages.

McCauley, Matthew, "Trocar Cannula Device with Retention Feature," U.S. Appl. No. 12/644,147, filed Dec. 22, 2009, 14 pages.

Zica, Michael, et al., "Viscous Fluid Extraction," U.S. Appl. No. 12/749,842, filed Mar. 30, 2010, 12 pages.

International Searching Authority, International Search Report of the International Searching Authority, International Application No. PCT/US2010/057582, Mar. 31, 2011, 5 pages.

International Searching Authority, Written Opinion of the International Searching Authority, International Application No. PCT/US2010/057582, Mar. 31, 2011, 7 pages.

ALCON®, Vitreoretinal Products Catalog, © 2008, 22 pages.

"The Grieshaber Trocar/Cannula Set," dated Aug. 1998, 2 pages.

Lopez, Jose Luis, et al., "Ophthalmic Valved Trocar Cannula," U.S. Appl. No. 12/951,266, filed Nov. 22, 2010, 30 pages.

* cited by examiner

OPHTHALMIC VALVED TROCAR CANNULA

PRIORITY CLAIM

This application claims the benefit of priority of U.S. Provisional Patent Application Serial No. 61/289,449, titled "OPHTHALMIC VALVED TROCAR CANNULA," filed on Dec. 23, 2009, whose inventors are Jose Luis Lopez, Anil K. Patnala, and Michael M. Martin, which is hereby incorporated by reference in its entirety as though fully and completely set forth herein.

FIELD OF THE INVENTION

The present invention generally pertains to ophthalmic surgery. More particularly, but not by way of limitation, the present invention pertains to ophthalmic trocar cannulas and vents.

DESCRIPTION OF THE RELATED ART

Microsurgical instruments may be used by surgeons for removal of tissue from delicate and restricted spaces in the human body, e.g., in surgery on the eye (such as procedures for removal of the vitreous body, blood, scar tissue, or the crystalline lens). Such instruments may include a control console and a surgical handpiece with which the surgeon dissects and removes the tissue. With respect to posterior segment surgery, the handpiece may be a vitreous cutter probe, a laser probe, or an ultrasonic fragmenter for cutting or fragmenting the tissue and may be connected to the control console by a long air-pressure (pneumatic) line and/or power cable, optical cable, or flexible tubes for supplying an infusion fluid to the surgical site and for withdrawing or aspirating fluid and cut/fragmented tissue from the site. The cutting, infusion, and aspiration functions of the handpiece may be controlled by the remote control console that not only provides power for the surgical handpiece(s) (e.g., a reciprocating or rotating cutting blade or an ultrasonically vibrated needle), but may also control the flow of infusion fluid and provide a source of vacuum (relative to atmosphere) for the aspiration of fluid and cut/fragmented tissue. The functions of the console may be controlled manually by the surgeon, (e.g., through use of a foot-operated switch or proportional control).

During posterior segment surgery, the surgeon may use several handpieces or instruments during the procedure. This procedure may require that these instruments be inserted into, and removed out of the incision. This repeated removal and insertion may cause trauma to the eye at the incision site. To address this concern, hubbed cannulae were developed at least by the mid-1980s. These devices may include a narrow tube with an attached hub. The tube may be inserted into an incision in the eye up to the hub, which may act as a stop, preventing the tube from entering the eye completely. The hub may be stitched to the eye to prevent inadvertent removal. Surgical instruments can be inserted into the eye through the tube, and the tube may protect the incision sidewall from repeated contact by the instruments. In addition, the surgeon may use the instrument, by manipulating the instrument when the instrument is inserted into the eye through the tube, to help position the eye during surgery. Disadvantages of prior art cannulae may include the height of the projection on the surface of the eye, as well as the lack of any means to control loss of intraocular pressure during instrument exchange or removal. The eye, being a pressurized globe, may expel aqueous or vitreous out of the open cannula when a surgical device is not present. With prior art cannulae, loss of intraocular pressure was prevented by the insertion of a plug or cap into the tube to seal the cannula and prevent the expression of fluid and tissue. This may be a time-consuming process that may require additional instrumentation as well as the assistance of other operating room personnel and may increase the risk of post-operative infection.

SUMMARY OF THE INVENTION

In various embodiments, a trocar cannula may be configured for insertion into an eye to facilitate insertion and removal of instruments during surgery. The cannula may be affixed to an overcap (affixed to inhibit rotation of the overcap relative to the cannula). The overcap may include a seal for inhibiting the flow of fluids out of the cannula (when an instrument is not inserted) while the cannula is inserted in the eye. In some embodiments, the seal may be molded into the overcap or may include a wafer that is fixed between the cannula and the overcap such that the seal does not rotate relative to the cannula and the overcap. In some embodiments, the cannula and overcap may snap together through a tab/slot interface in a permanent fashion such that the cannula and overcap may not be separated without damaging at least part of the cannula or overcap. In some embodiments, a vent cannula may be slidably receivable in the slit of the seal for allowing fluids to vent from the eye through the cannula. In some embodiments, the cannula may include at least one indentation to frictionally engage a portion of the vent when the vent is inserted into the cannula.

BRIEF DESCRIPTION OF THE DRAWINGS

For a more complete understanding of the present invention, reference is made to the following description taken in conjunction with the accompanying drawings in which.

It is to be understood that both the foregoing general description and the following detailed description are exemplary and explanatory only and are intended to provide a further explanation of the present invention as claimed.

DETAILED DESCRIPTION OF THE EMBODIMENTS

Figure 1:
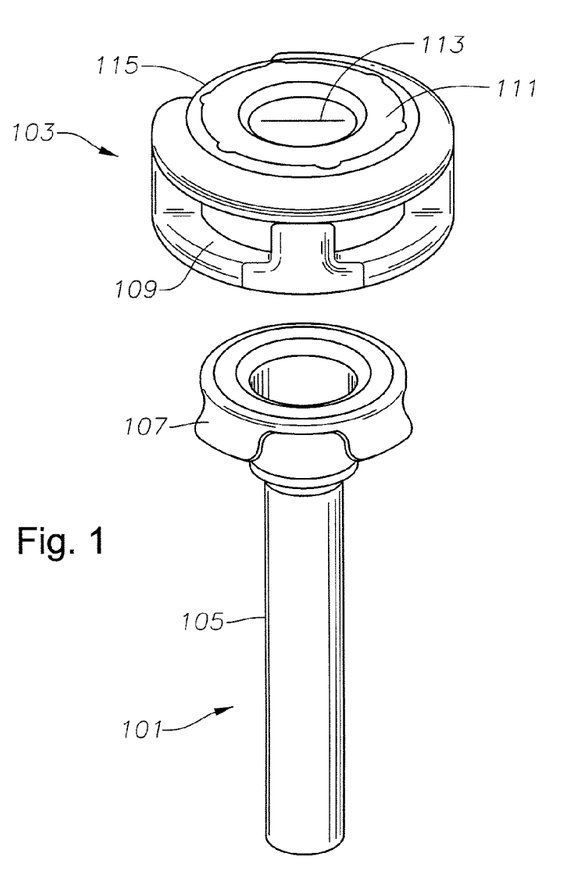
FIG. 1 illustrates a cannula and an overcap, according to an embodiment.

FIG. 1 illustrates an embodiment of a trocar cannula 101 and an overcap 103. The trocar cannula 101 may be configured for insertion into an eye to facilitate insertion and removal of instruments during surgery. The cannula 101 may include a shaft 105 capable of extending into the eye (e.g., through a sclera, conjunctiva, etc). In some embodiments, the cannula 101 may be attached to an overcap 103. For example, the cannula 101 may include one or more tabs 107 configured to engage corresponding slots 109 on the cannula 101 (e.g., the cannula 101 illustrated in FIG. 1 includes four tabs 107 to engage four corresponding slots 109 on the overcap 103). Other attachments are also contemplated. For example, the cannula 101 may include the slots and the overcap may include the tabs. In some embodiments, the cannula 101 may be attached to the overcap 103 through adhesive, thermal bonding, etc. In some embodiments, a seal 111 may be coupled to the overcap 103 (e.g., the seal 111 may be disposed at least partially between the shaft 105 and the overcap 109) to form an overmolded valve. As shown in FIG. 1, a surface of the seal 111 may be exposed on the overcap 109. In some embodiments, the exposed surface of the seal 111 may include one or more slits 113 to allow passage of surgical tools into the cannula 101. In the absence of a surgical instrument, the seal 111 may inhibit fluid flow through the seal 111.

Figure 2:
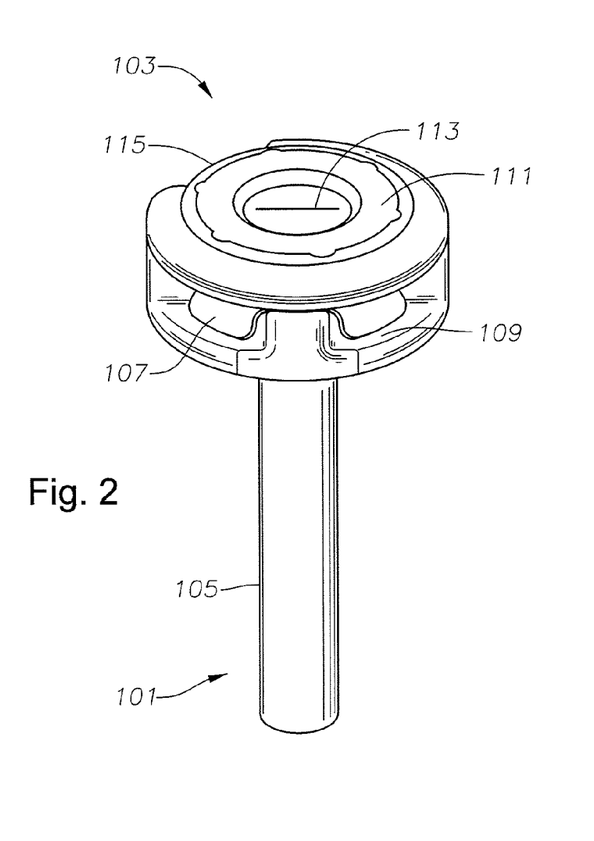
FIG. 2 illustrates the cannula affixed to the overcap, according to an embodiment.

FIG. 2 illustrates an embodiment of the cannula 101 affixed to the overcap 103 (e.g., after engagement of the tabs 107 in respective slots 109). In some embodiments, the tab/slot interface may prevent rotation of the overcap 103 relative to the cannula 101 (e.g., during insertion of the cannula 101 into the eye). In some embodiments, the tabs 107 may be configured to permanently hold the overcap 103 to the cannula 101 (such that the overcap 103 may not be removed from the cannula 101 without destroying part of the cannula 101 and/or overcap 103). For example, the tabs 107 (and cannula 101) may be made of stainless steel and the overcap 103 may be made of plastic (e.g., polycarbonate). Other materials are also contemplated. The permanent hold between the overcap 103 and the cannula 101 may prevent inadvertent removal of the overcap 103 from the cannula 101 during surgery (e.g., vitreoretinal surgery).

Figure 3A:
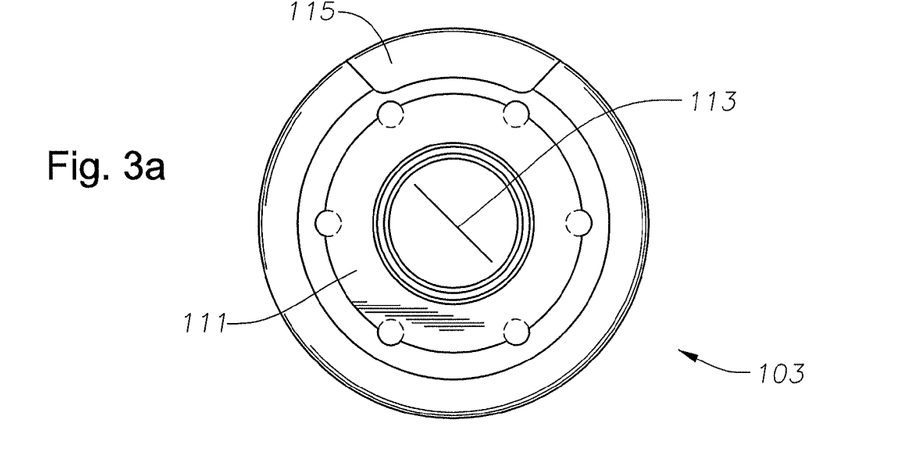
FIG. 3a illustrates a top view showing the slit in the seal on the overcap, according to an embodiment.
Figure 3B:
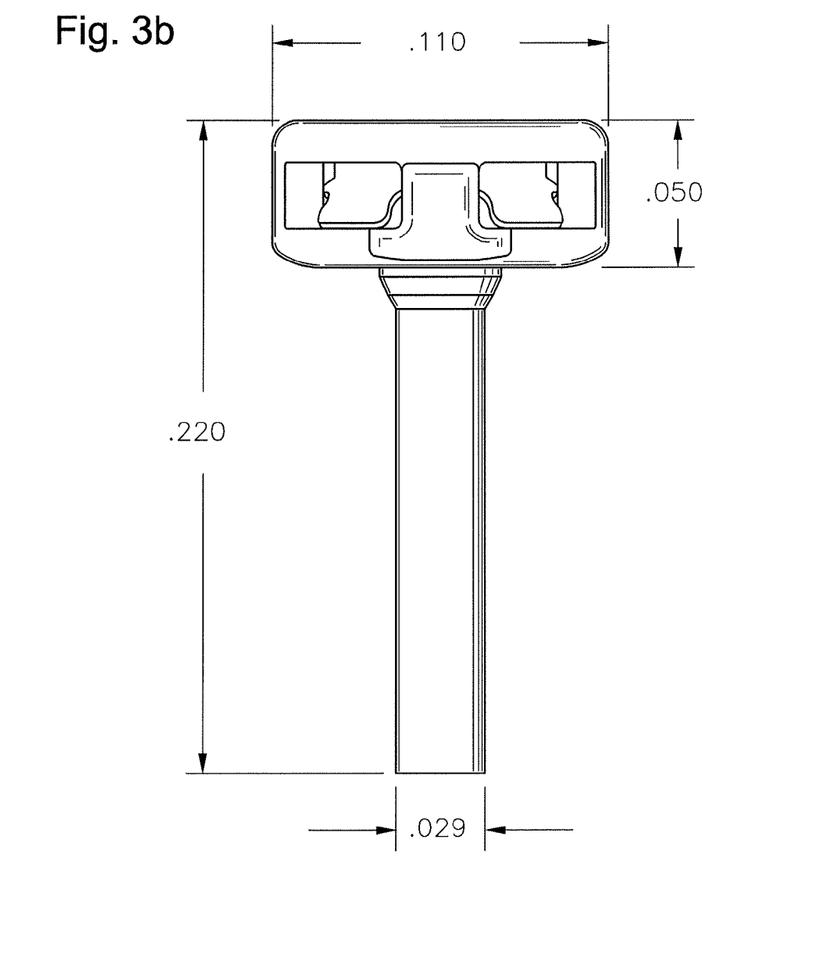
FIG. 3b illustrates a side view of the cannula and overcap with several example dimensions, according to an embodiment.

FIG. 3a illustrates a top view of an embodiment of the slit 113 in the seal 111 on the overcap 103. FIG. 3b illustrates a side view of an embodiment of the cannula 101 and overcap 103 with several example dimensions (provided in inches). Other dimensions are also contemplated. For example, while the outer diameter of the cannula 101 is shown as 0.029 inches (corresponding to a 23 gauge cannula), in another embodiment, the outer diameter of the cannula may be 0.0243 inches (for a 25 gauge cannula). Other outer diameters are also contemplated.

Figure 4A:
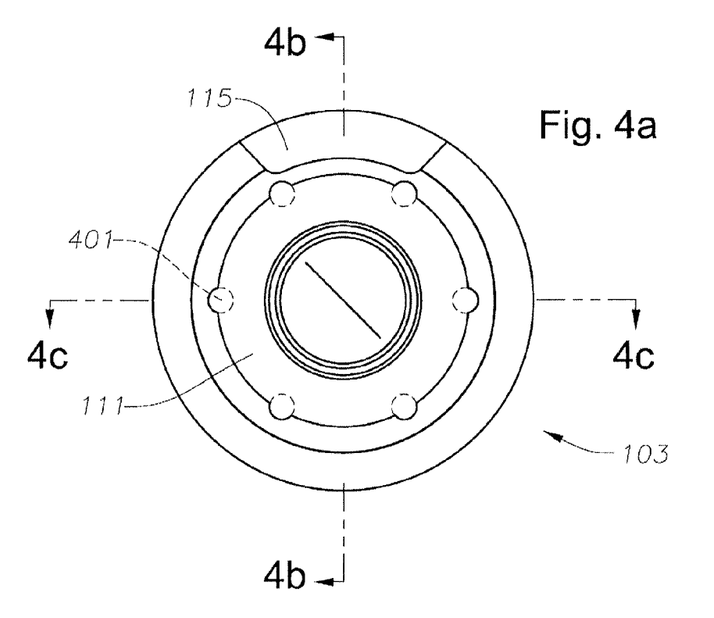
FIGS. 4a-d illustrate cross-sections of embodiments of the overcap and seal.
Figure 4B:
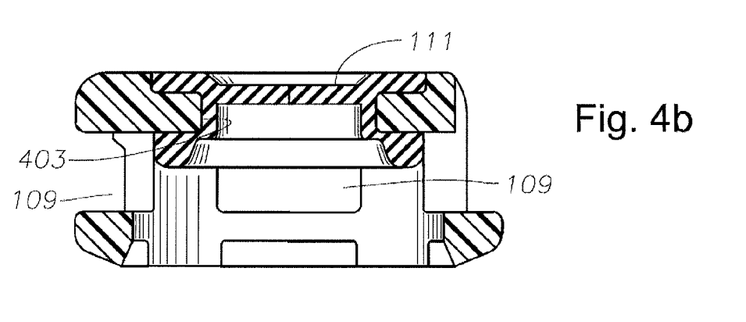
Figure 4C:
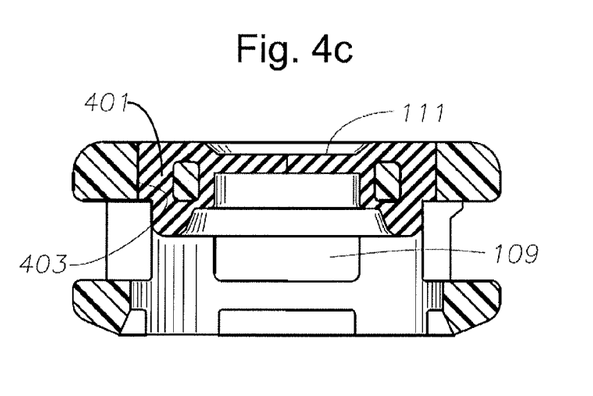
Figure 4D:
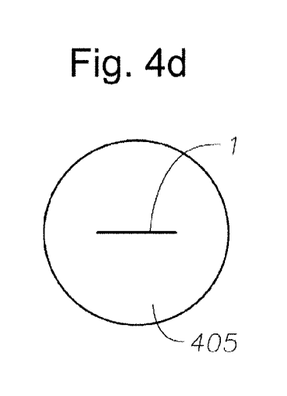

FIGS. 4a-c illustrate cross-sections of an embodiment of the overcap 103 and seal 111. The seal 111 may be made of an elastomer (e.g., silicone). In some embodiments, the seal 111 may be attached to the overcap 103 to inhibit rotation of the seal 111 relative to the overcap 103. For example, the seal 111 may be overmolded into a depression 403 and one or more holes 401 in the overcap 103. In some embodiments, the seal 111 may include a silicon wafer 405 that is formed separately from the overcap 103 and inserted between the overcap 103 and the cannula 101 during assembly of the overcap 103 onto the cannula 101. In such a case, the seal 111 may be attached to the overcap 103 and cannula 101 through a friction fit. Other attachments are also contemplated (e.g., adhesive).

Figure 5A:
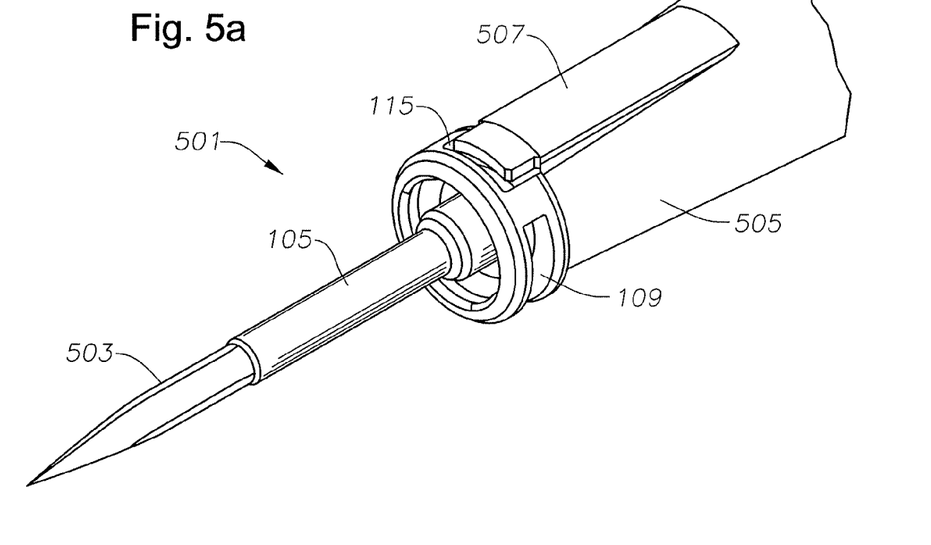
FIG. 5a illustrates the cannula on a trocar inserter, according to an embodiment.
Figure 14:
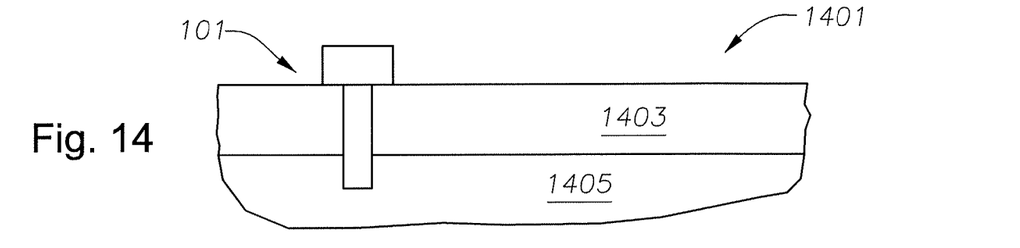
FIG. 14 illustrates a valved trocar cannula inserted into an eye, according to an embodiment.

FIG. 5a illustrates an embodiment of the cannula 101 on a trocar inserter 501. In some embodiments, the trocar inserter 501 may include a trocar blade 503 attached to a handle 505. In some embodiments, the handle 505 may be made of plastic and the blade 503 may be made of stainless steel. Other materials are also contemplated. The trocar blade 503 may extend past the end of the shaft 105 and may include one or more sharp edges to pierce an eye 1401 (e.g., pierce a hole through the sclera 1403 and into the vitreous body 1405) for insertion of the cannula 101. In some embodiments, a guide 507 may fit into guide slot 115 to inhibit rotation of the overcap 103/cannula 101 relative to the handle 505 during insertion of the cannula 101 into eye 1401. In some embodiments, the guide 507 may releasably engage the guide slot 115 such that when the trocar inserter 501 is withdrawn from the overcap 103/cannula 101, the guide 507 does not pull the overcap 103/cannula 101 out of the eye 1401. For example, the guide 507 may frictionally engage the guide slot 115 with a friction force that is less than a friction force exerted by the eye on the external sides of the cannula 101 when the cannula 101 is in the eye.

Figure 5B:
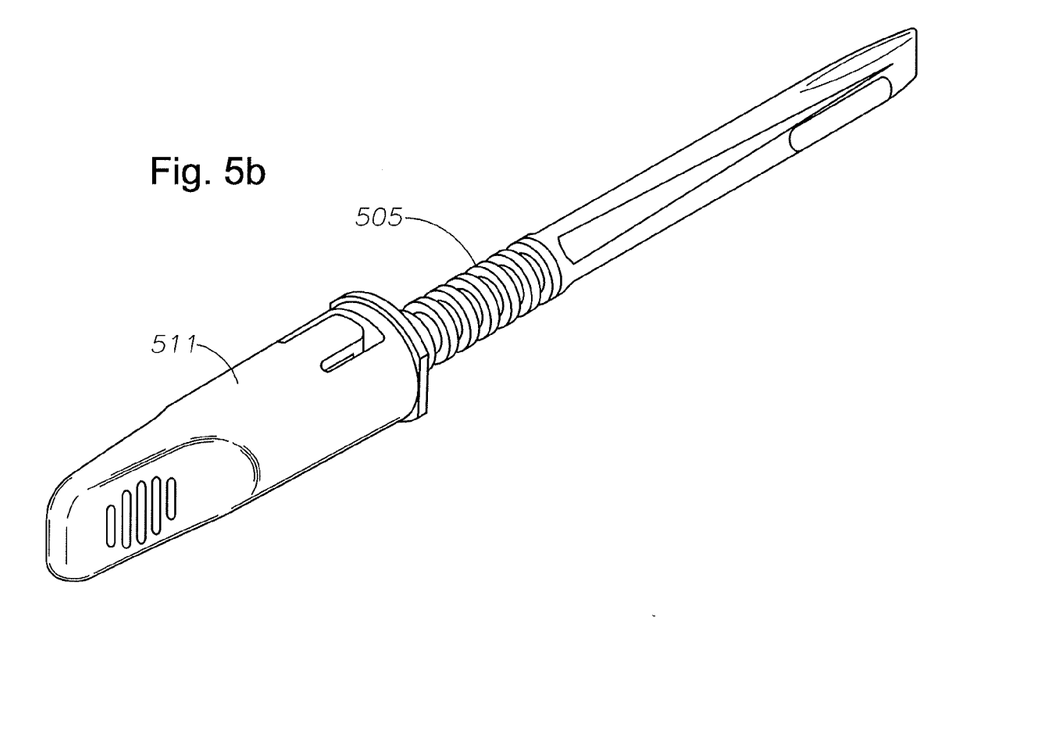
FIG. 5b illustrates the cannula on a trocar inserter with a shipping cap, according to an embodiment.

While the guide 507 is depicted as a tab to be received into guide slot 115, other interlocking features are also contemplated. For example, the guide 507 and guide slot 115 may include different interlocking features (such as a ring and a rod) or may include other interlocking components (e.g., interlocking magnets (one on each of the handle and overcap 103), engaging o-rings (one on each of the handle and overcap 103), etc). In some embodiments, the guide 507/guide slot 115 interaction may prevent rotation between the cannula 101 and the overcap 103 so that any angular movement of the trocar handle 505 about the handle's axis may be transmitted to the overcap 103 and then to the cannula 101. This interaction may provide vitreoretinal surgeons angular control of the cannula 101 relative to the trocar handle 505 during insertion of the cannula 101 into the sclera 1403. FIG. 5b illustrates an embodiment of the cannula 101 on a trocar inserter 501 with a shipping cap 511 (which may be snapped on over the cannula 101 and/or over the trocar inserter 501 to protect the cannula 101 and/or trocar inserter 501.

Figure 6A:
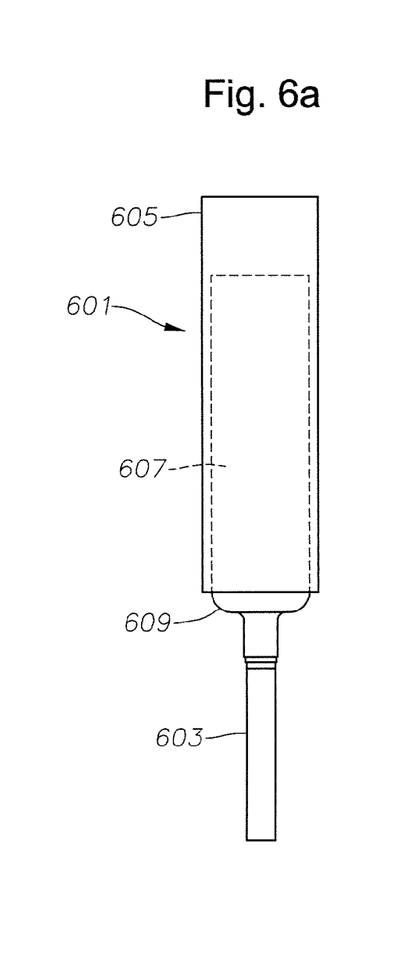
FIGS. 6a-b illustrates a vent, according to an embodiment.
Figure 6B:
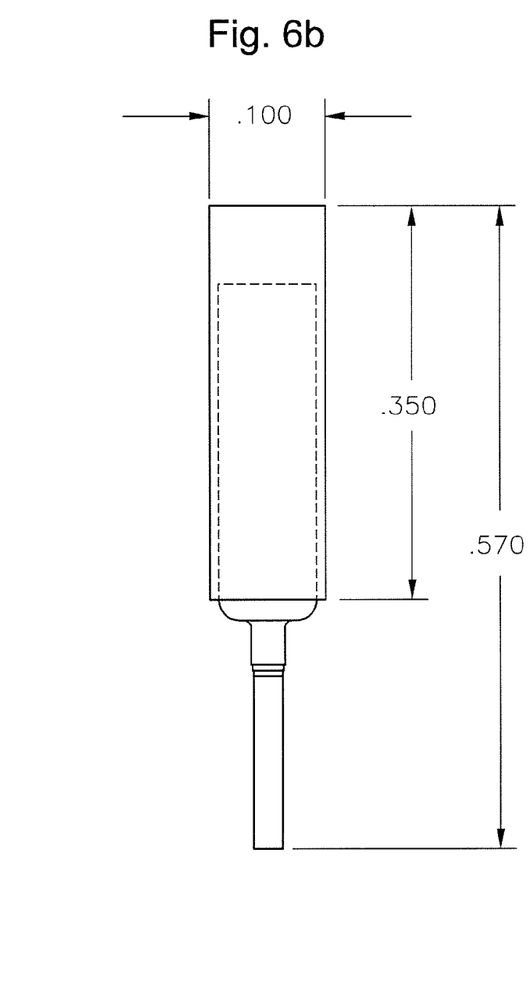
Figure 7:
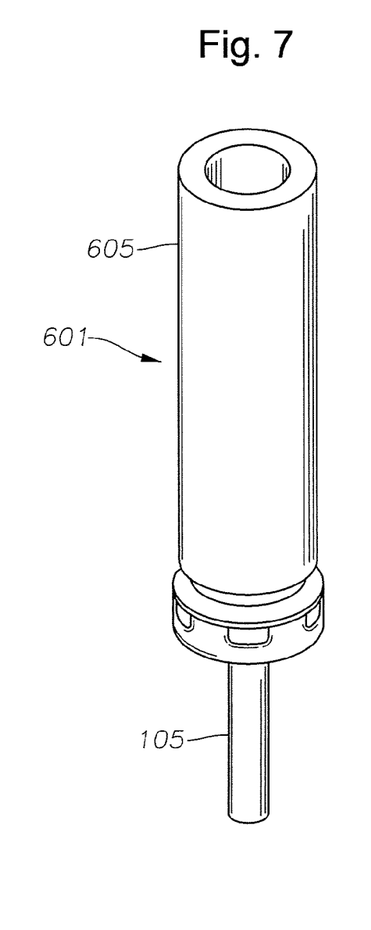
FIG. 7 illustrates a vent in the valved trocar cannula, according to an embodiment.

FIGS. 6a-b illustrates an embodiment of a vent 601. While the seal 111 of the valved trocar cannula may close off the cannula from fluid flow into or out of the cannula when, for example, a surgical instrument is occluding the cannula, a vent cannula 603 may be configured to slide into the slit 113 of the seal 111 to allow fluids to vent from the eye through the cannula 101 (e.g., see FIG. 7). In some embodiments, the vent 601 may hold the seal 111 in an open position to allow fluid (e.g., a gas or liquid) to vent through the cannula 101. For example, a gas (or another fluid) may flow through the cannula 101 and out of vent 601 during a procedure to replace the gas with another fluid. The vent 601 may further include a rim 609 to provide a stop for preventing the vent from slipping all the way into the seal 111. The vent cannula 603 may have an outer diameter that is smaller than an inner diameter of trocar cannula 101 to allow the vent cannula 603 to slide past the seal 111 and into the trocar cannula 101. The vent cannula 603 may further include a rim 609 with at least one dimension that is large enough to prevent the vent 601 from slipping completely into the trocar cannula 101 (e.g., the diameter of the rim 609 may be larger than an inner diameter of the trocar cannula 101).

In some embodiments, the vent 601 may be a separate device from the cannula to allow the vent 601 to be inserted and removed without adding or removing parts of the cannula 101 (e.g., without having to remove the overcap 103 of the cannula 101). The size of the vent 601 may also allow a user (e.g., a surgeon) to handle the vent 601 with fingers (or, for example, forceps) during the insertion and removal of the vent 601.

In some embodiments, the vent 601 may include a flexible tube 605 (e.g., a silicone tube) frictionally engaging the vent cannula 603. The tube 605 may provide a visual indicator (e.g., be at least partially transparent) of the venting process (e.g., if a substance is overflowing from the eye (such as silicone during a viscous fluid control injection procedure), the silicone may flow into the tube 605 and be visible to a user. In some embodiments, the tube 605 may be used as a grasping surface for vent removal from the cannula 101 (e.g., to assist grasping by fingers or forceps). Vent cannula 603 may include a tube portion 607 configured to receive the flexible tube 605 along an outer perimeter of the tube 607 (which may be made of, for example, stainless steel). In some embodiments, the tube 607 and vent cannula 603 may be formed of one piece. FIG. 6b illustrates several example dimensions (provided in inches), according to an embodiment. Other dimensions are also contemplated. In some embodiments, the dimensions of the vent 601 may allow for the passage of instruments through the vent 601 when the vent 601 is in seal 111.

Figure 8:
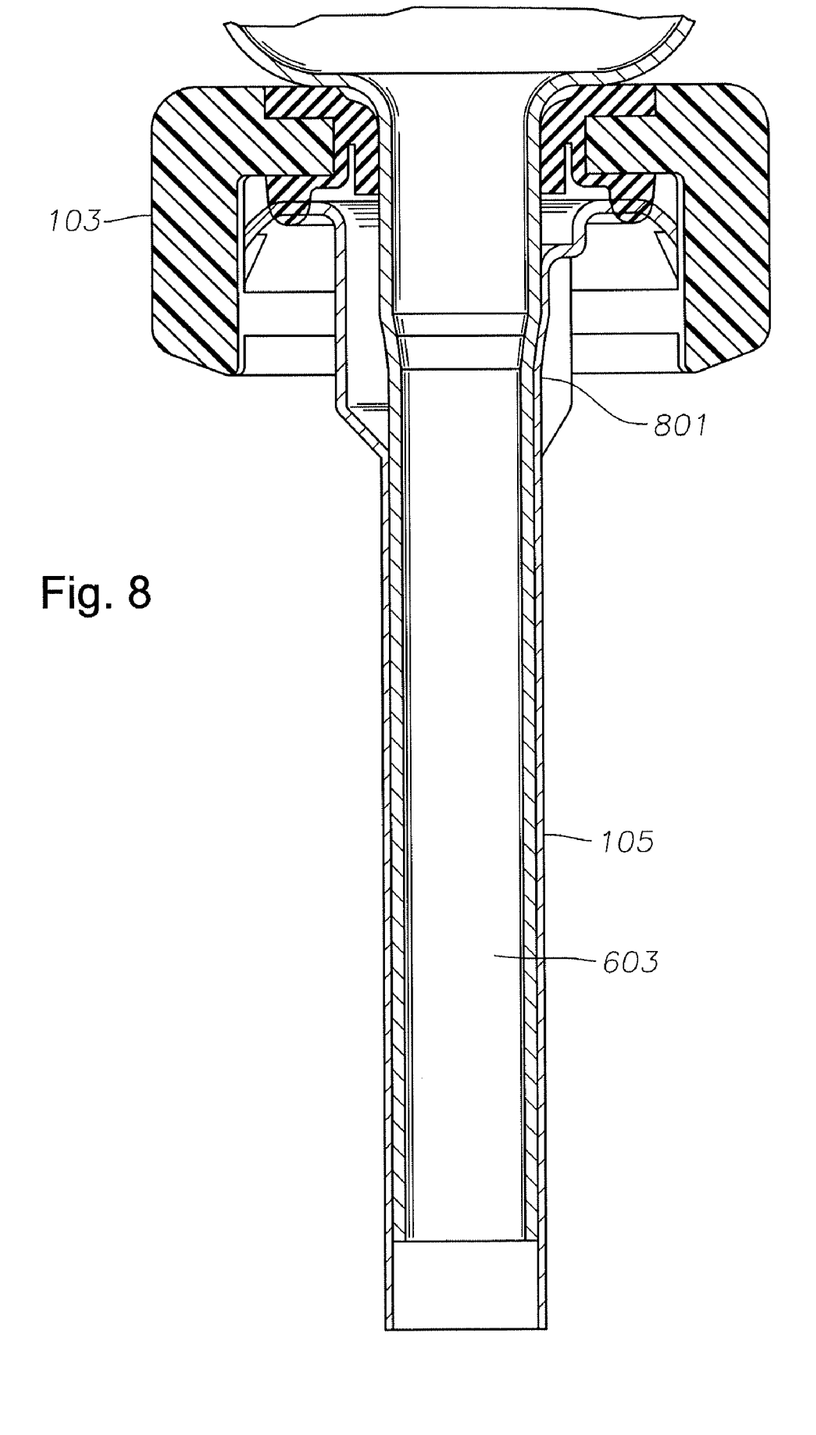
FIG. 8 illustrates a cross section of the vent in the valved trocar cannula, according to an embodiment.

FIG. 8 illustrates a cross section of an embodiment of the vent 601 in the cannula 101. In some embodiments, the cannula 101 may include at least one indentation 801 to frictionally engage a portion of the vent cannula 603 when the vent 601 is inserted into the cannula 101. The indentation 801 may be dimensioned to provide enough resistance to the vent 601 to keep the vent 601 in place during a procedure. In some embodiments, the resistance between the indentation 801 and vent 601 may be less than needed to pull the cannula 101 out of the eye when withdrawing the vent 601 from the cannula 101 (such that the cannula 101 is not pulled out of the eye when the vent 601 is pulled out of the cannula 101 while the cannula 101 is in the eye).

Figure 9A:
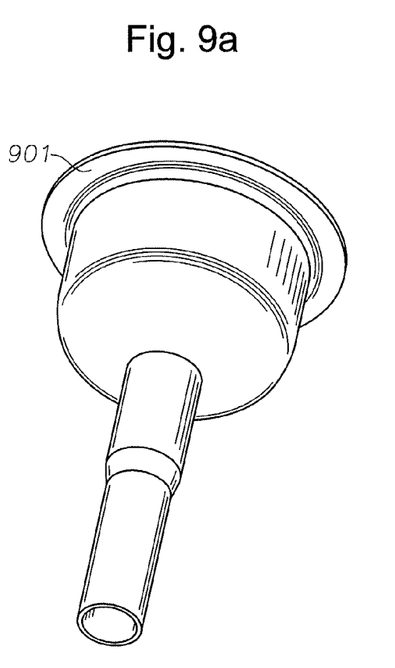
FIGS. 9a-b illustrate a second embodiment of a vent.
Figure 9B:
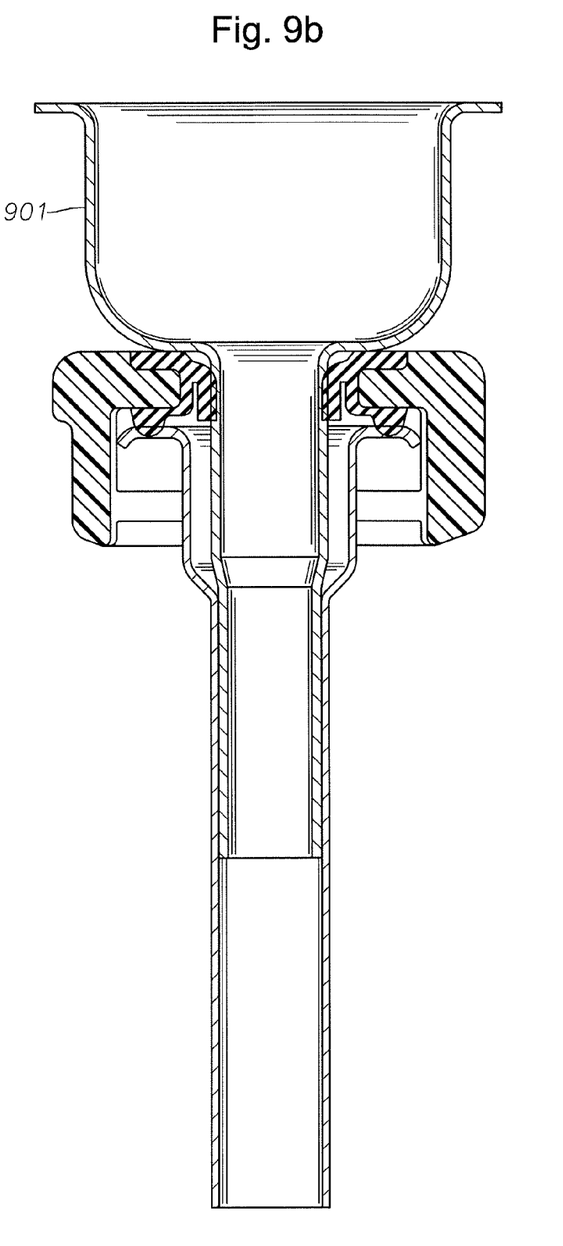
Figure 10A:
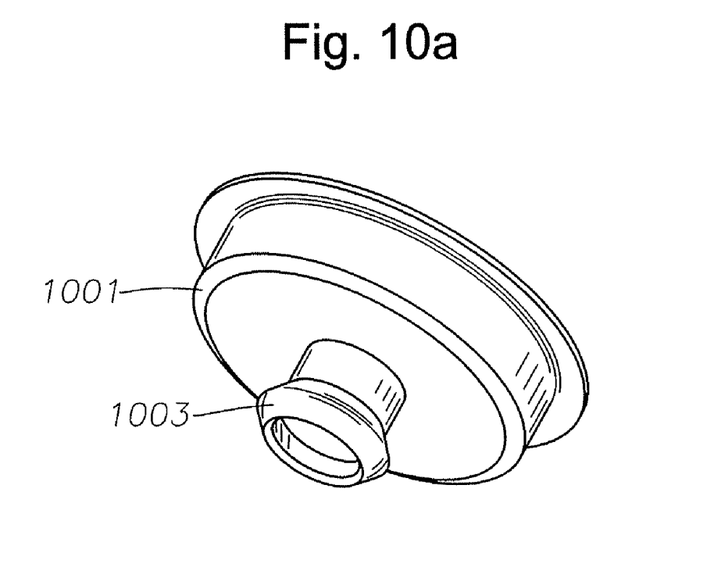
FIGS. 10a-c illustrate a third embodiment of a vent.
Figure 10B:
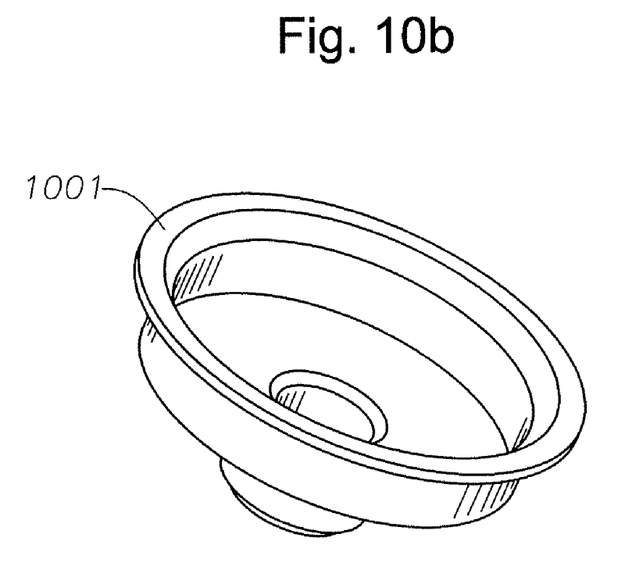
Figure 10C:
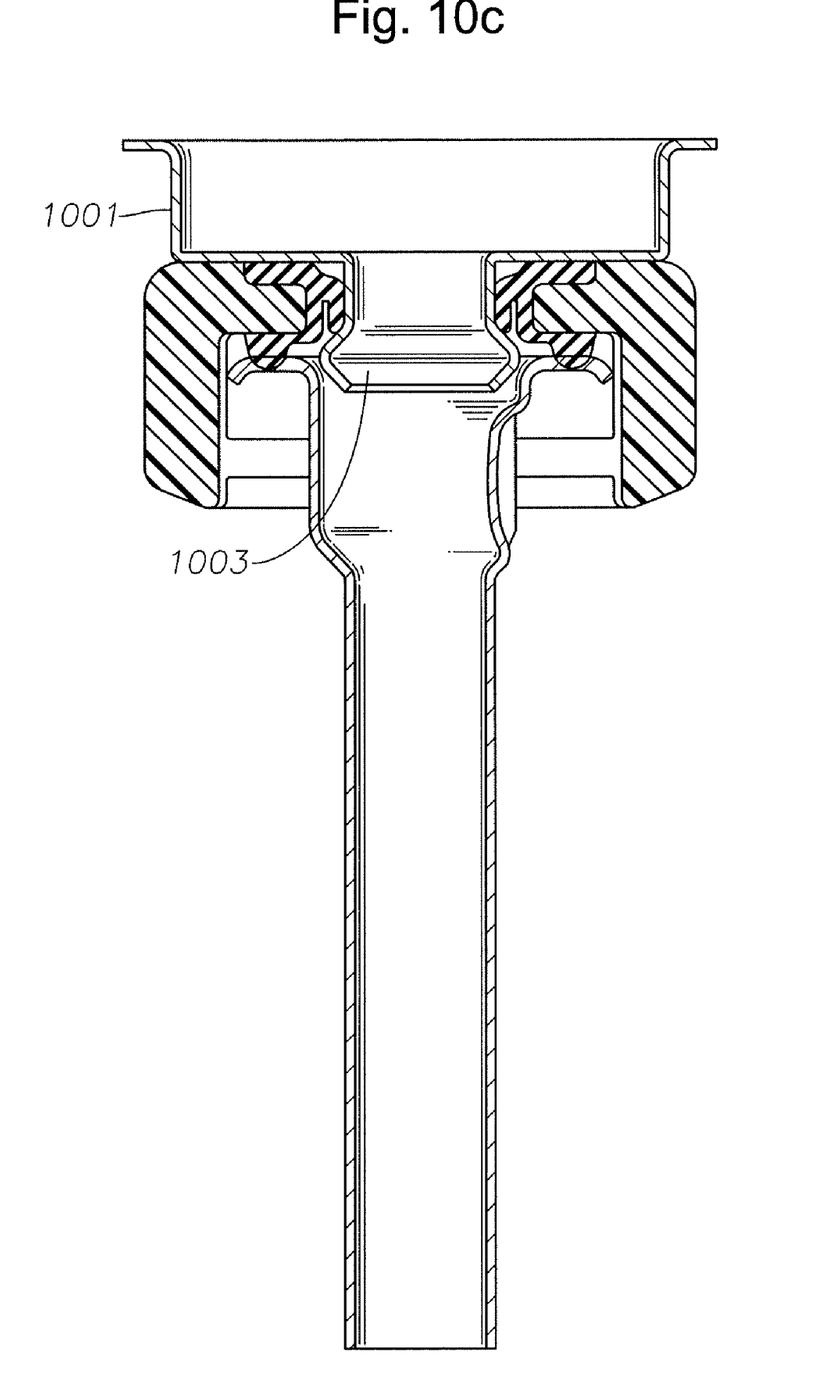

Other embodiments of the vent are also contemplated. For example, an embodiment of a vent 901 is shown in FIGS. 9a-b. As seen in FIGS. 9a-b, the vent 901 may not include a tube 605, but may instead be a single piece. The vent 901 may be deep drawn and may include a retention feature for mating with a retention feature on a cannula 101. Other formation techniques are also contemplated (e.g., the vent 901 may be molded). In some embodiments, the vent may not include a retention feature. Yet another embodiment is shown as vent 1001 in FIGS. 10a-c. Vent 1001 may include a large bell shaped inlet that may make it easier to insert and remove tools through the vent 1001 when the vent 1001 is inserted into a cannula 101. The vent 1001 may also include one or more retention features 1003 to increase a grip between the vent 1001 and a cannula 101 when the vent 1001 is inserted into a cannula 101.

Figure 11:
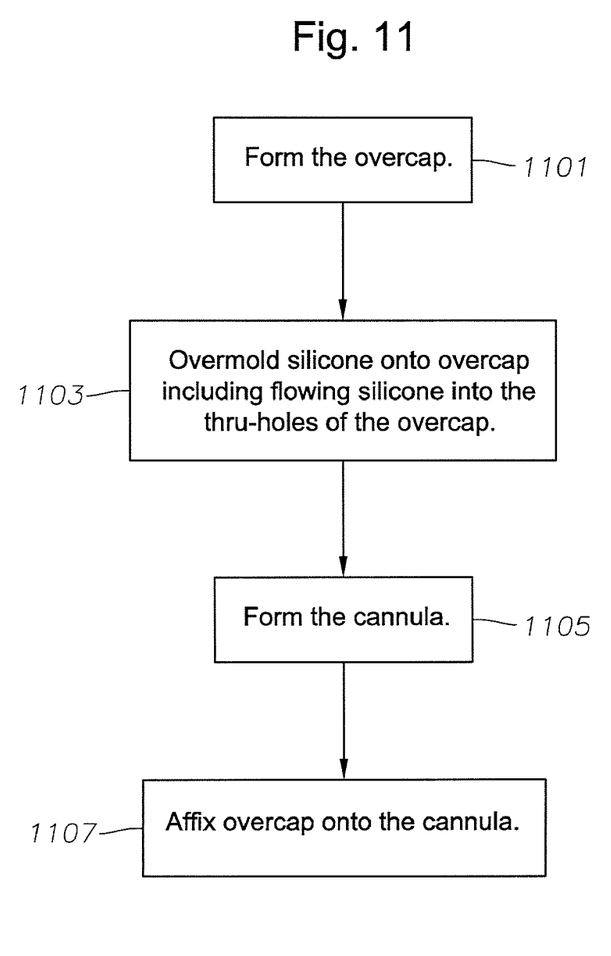
FIG. 11 illustrates a flowchart of a method for forming the valved trocar cannula, according to an embodiment.

FIG. 11 illustrates a flowchart of a method for forming the valved trocar cannula, according to an embodiment. The elements provided in the flowchart are illustrative only. Various provided elements may be omitted, additional elements may be added, and/or various elements may be performed in a different order than provided below.

At 1101, the overcap 103 may be formed. For example, the overcap 103 may be molded to include thru-holes 401 for receiving a silicone seal 111. Molding processes for the overcap 103 may include injection molding, compression molding, blow molding, rotational molding, etc. Other techniques for forming the overcap 103 are also contemplated (e.g., casting).

At 1103, the seal 111 may be overmolded onto the overcap 103. For example, the seal 111 may include an elastomer (such as silicone) molded into a depression 403 of the overcap 103 and may flow into holes 401 to secure the seal 111 to the overcap 103. In some embodiments, the overcap 103 may be placed into a mold that defines spaces through the overcap 103 for the seal 111. The elastomer may then be injected into the mold and flow through the defined spaces through the overcap 103 to form the seal 111 in the overcap 103. Other manufacturing processes are also contemplated. For example, the seal 111 and overcap 103 may be molded as one piece (e.g., using the same material for both the overcap 103 and seal 111 in a single mold). In some embodiments, the seal 111 may be formed separately from the overcap 103 (e.g., see FIG. 10). In some embodiments, the seal may be formed with a slit 113 or the slit 113 may be formed in the seal 111 after the seal is formed (e.g., the slit 113 may be cut into the seal 111 using a sharp edge).

At 1105, a cannula 101 may be formed. For example, the cannula 101 may be deep drawn. Deep drawing the cannula 101 may include starting with a disc of material that is pressed between one or more sets of male/female dies to deep draw the cannula 101. A final step in cannula formation may include removing excess material and/or polishing the cannula 101. In some embodiments, material between the tabs 107 may be sheared off between a male and female die or may be removed in other ways (e.g., cut away). In some embodiments, the cannula 101 may be molded (e.g., injection molding, compression molding, blow molding, rotational molding, extrusion molding, etc). Other techniques for cannula formation are also contemplated. In some embodiments, the cannula 101 may be made of stainless steel or plastic. Other materials may also be used. In some embodiments, the cannula 101 may be formed with snapping tabs 107. For example, the dies or mold for the cannula 101 may include spaces for the formation of the tabs or the tabs may be formed on the cannula 101 through machining. Other tab forming techniques are also contemplated.

At 1107, the overcap 103 may be affixed to the cannula 101. For example, the tabs 107 may be snapped into corresponding slots 109. In some embodiments, the overcap 103 may slightly deform to receive the tabs 107 or the tabs 107 may be configured to slightly deform as the overcap 103 is pressed onto the cannula 101 and then return to their initial condition as the corresponding slots 109 of the overcap 103 pass over the tabs 107. The tabs 107 may be rigid enough (e.g., made of stainless steel) such that the overcap 103 may not be removed from the cannula 101 without destroying part of the cannula 101 and/or overcap 103.

Figure 12:
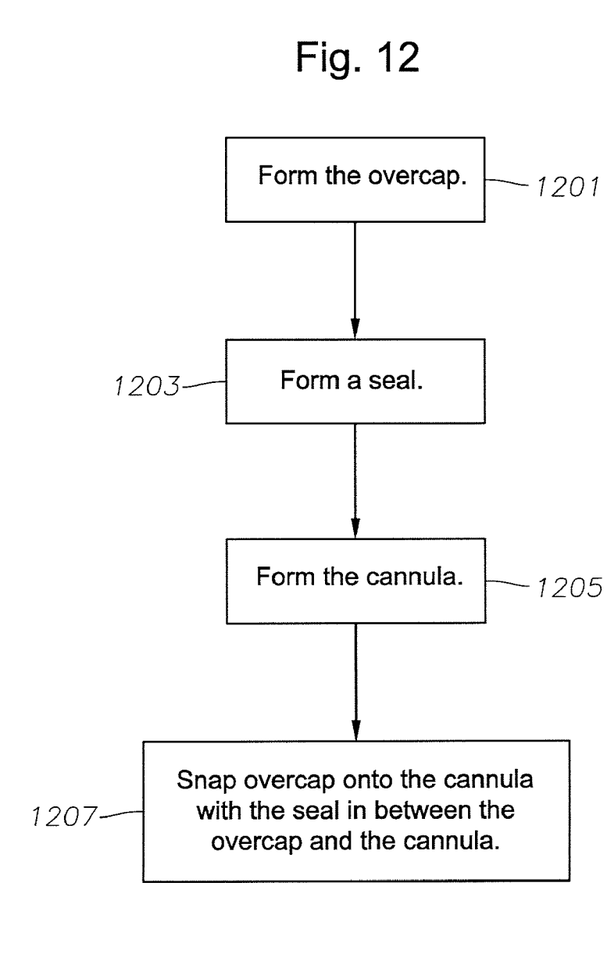
FIG. 12 illustrates a flowchart of a method for forming the valved trocar cannula, according to another embodiment.

FIG. 12 illustrates a flowchart of a method for forming the valved trocar cannula according to another embodiment. The elements provided in the flowchart are illustrative only. Various provided elements may be omitted, additional elements may be added, and/or various elements may be performed in a different order than provided below.

At 1201, an overcap 1103 may be formed (e.g., through molding). In some embodiments, the overcap 1103 may be formed with receiving slots 109.

At 1203, a seal 111 (such as a silicone wafer 405) may be formed. In some embodiments, the silicone wafer 405 may be molded with a slit 113 or the slit 113 may be formed in the silicone wafer 405 after molding (e.g., the slit 113 may be cut into the silicone wafer using a sharp edge).

At 1205, the cannula 101 may be formed. For example, the cannula 101 may be molded out of stainless steel and may include tabs 107.

At 1207, the silicone wafer 405 may be inserted between the cannula 101 and overcap 103 and the overcap 103 may be affixed to the cannula 101 (e.g., the overcap 103 may be snapped onto the cannula 101 such that the slots 109 may receive tabs 107).

Figure 13:
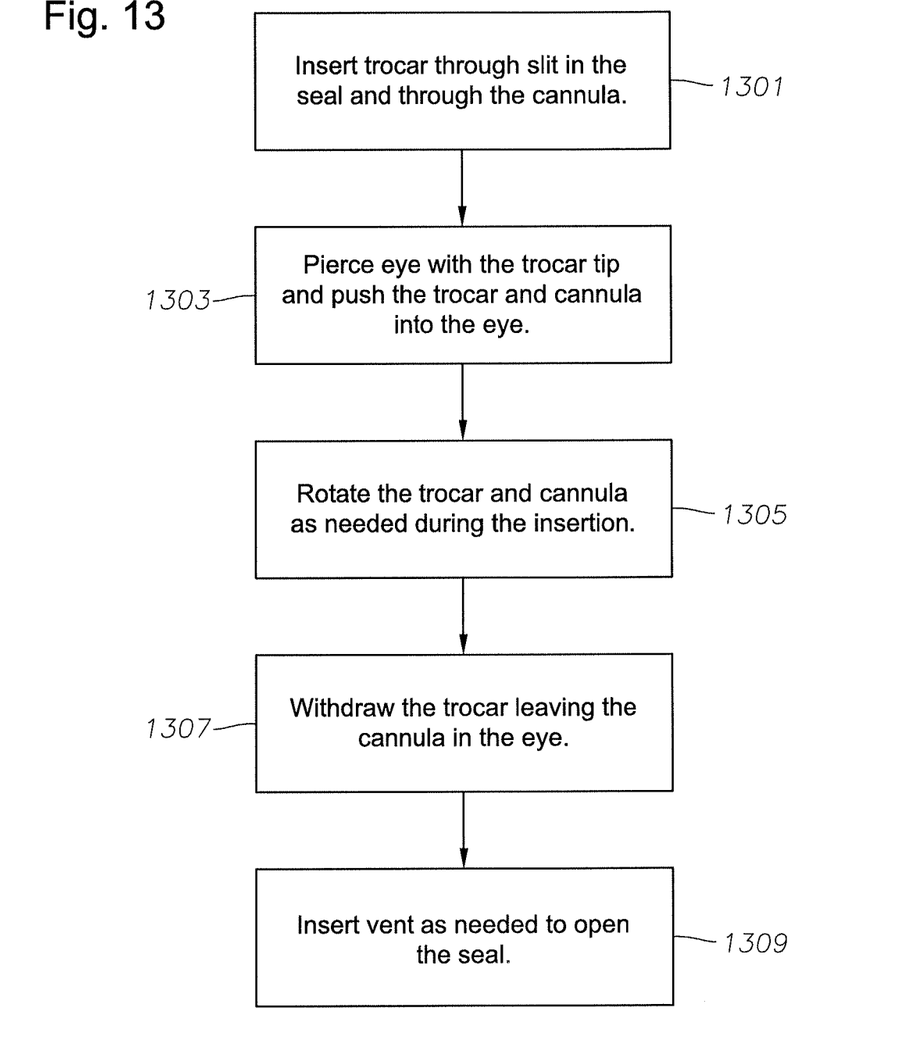
FIG. 13 illustrates a flowchart of a method for using the vent with the valved trocar cannula, according to an embodiment.

FIG. 13 illustrates a flowchart of a method for using the vent with the valved trocar cannula, according to an embodiment. The elements provided in the flowchart are illustrative only. Various provided elements may be omitted, additional elements may be added, and/or various elements may be performed in a different order than provided below.

At 1301, the trocar blade 503 may be inserted through the slit 113 in the seal 111 and through cannula 101. At 1303, the eye 1401 may be pierced with the trocar blade 503 and the cannula 101 may be pushed into the eye. At 1305, the trocar blade 503 and cannula 101 may be rotated as needed during the insertion. At 1307, the trocar blade 503 may be withdrawn leaving the cannula 101 in the eye 1401. At 1309, a vent 601 may be inserted as needed to open the seal 111 to allow fluid/gas to vent through the cannula 101 and out of the eye 1401. The vent 601 may be removed and/or reinserted as needed into the seal 111 and cannula 101 without withdrawing the cannula 101 from the eye during the procedure. Inserting the withdrawing the vent 601 may be performed using, for example, the user's fingers or a pair of forceps.

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An apparatus, comprising:
    a single-piece cannula configured for insertion into an eye, wherein the cannula includes at least two tabs;
    an overcap affixed to the cannula, wherein the overcap is configured not to rotate relative to the cannula, wherein the overcap includes at least two slots and wherein the overcap is affixed to the cannula by receiving the at least two tabs in the corresponding at least two slots; and
    a seal between the cannula and the overcap, wherein the seal is configured to allow passage of a surgical tool into the cannula through a slit in the seal while inhibiting fluid flow through the seal when the surgical tool is not present in the seal;
        wherein the seal is overmolded into a depression in the overcap; and
        wherein the seal is molded into at least two holes in the overcap.

2. The apparatus of claim 1, further comprising a vent cannula configured to slide into the slit of the seal for allowing fluids to vent from the eye through the cannula.

3. The apparatus of claim 2, wherein the cannula comprises at least one indentation to frictionally engage a portion of the vent cannula when the vent cannula is inserted into the cannula.

4. The apparatus of claim 1, wherein the seal is molded into at least three holes in the overcap, wherein the three holes are positioned around a central main hole in the overcap for passage of the surgical tool.

5. The apparatus of claim 1, wherein the seal is molded into at least six holes in the overcap, wherein the six holes are arranged in a circle around a central main hole in the overcap for passage of the surgical tool.

6. The apparatus of claim 1, wherein the overcap comprises a guide slot, wherein the guide slot is configured to receive a guide tab from a trocar handle and wherein interaction between the guide slot and the guide tab inhibit rotation of the overcap relative to the handle during insertion of the cannula into the eye.

7. The apparatus of claim 1, wherein the at least two tabs are on an outer circumference of the cannula.

8. The apparatus of claim 1, wherein the at least two tabs are separated by a space such that the at least two tabs are configured to snap into separate slots of the at least two slots.

9. The apparatus of claim 8, wherein the at least two slots are separated by a portion of the overcap that is configured to occupy the space separating the at least two tabs when the overcap is snapped onto the cannula.

10. The apparatus of claim 1, wherein the at least two tabs comprises three tabs equally spaced around an outer circumference of the cannula.

11. The apparatus of claim 10, wherein the three tabs are configured to snap into three corresponding slots of the overcap.

12. The apparatus of claim 1, further comprising a vent cannula configured to slide into the slit of the seal for allowing fluids to vent from the eye through the cannula;
    wherein the cannula comprises at least one indentation to frictionally engage a portion of the vent cannula when the vent cannula is inserted into the cannula.

13. The apparatus of claim 1, wherein the guide slot is along an outer circumference of the overcap.

14. The apparatus of claim 1, wherein the guide tab extends from an outer circumference of the trocar handle.

15. The apparatus of claim 1, wherein the single-piece cannula comprises a flat top surface with the at least two tabs along the perimeter of the top surface and a chamfered edge on an inner edge of the top surface leading to an interior of the cannula.

* * * * *